United States Patent [19]

Lodder et al.

[11] Patent Number: 5,441,053
[45] Date of Patent: Aug. 15, 1995

[54] APPARATUS AND METHOD FOR MULTIPLE WAVELENGTH OF TISSUE

[75] Inventors: Robert A. Lodder; Lisa A. Cassis, both of Nicholasville, Ky.

[73] Assignee: University of Kentucky Research Foundation, Lexington, Ky.

[21] Appl. No.: 945,020

[22] Filed: Sep. 15, 1992

Related U.S. Application Data

[63] Continuation-in-part of Ser. No. 695,104, May 3, 1991, abandoned.

[51] Int. Cl.⁶ ................................. A61B 6/00
[52] U.S. Cl. .................................. 128/664; 128/634
[58] Field of Search ............... 128/664, 395–398, 128/633, 634, 665; 606/3, 15, 16; 607/88, 89, 90, 92, 93

[56] References Cited

U.S. PATENT DOCUMENTS

| | | | |
|---|---|---|---|
| 4,515,165 | 5/1985 | Carroll | 128/664 |
| 4,975,581 | 12/1990 | Robinson et al. | 128/633 |
| 5,088,493 | 2/1992 | Giannini et al. | 128/664 |
| 5,106,387 | 4/1992 | Kittrell et al. | 128/664 |

FOREIGN PATENT DOCUMENTS

0649410  3/1979  U.S.S.R. ................ 128/664

Primary Examiner—Ruth S. Smith
Attorney, Agent, or Firm—King & Schickli

[57] ABSTRACT

An apparatus for analyzing the chemical composition of tissue includes a near infrared light source, a fiber-optic probe, a mechanism for directing the light from the light source onto the tissue and detectors for detecting light reflected by the tissue. The light source transmits an incident beam having a wavelength ranging from 1000 to 2500 nm. A compound parabolic concentrator (CPC) is connected to a distal end of the fiber optic probe to focus or concentrate the wavelengths of light simultaneously and in parallel on a particular spot of tissue. Alternatively, an inverted, substantially conical reflector is positioned to scatter the incident light across the tissue. The method includes the steps of (1) focusing light onto the tissue to be analyzed; (2) detecting light reflected by the tissue; and (3) analyzing the resulting spectra across the full wavelength of the originally focused light. A color image is then produced for subsequent study.

8 Claims, 5 Drawing Sheets

APPARATUS AND METHOD FOR MULTIPLE WAVELENGTH OF TISSUE

This invention was made with government support under NSF RII-8610671 and NIH BRSG S07 RR05857-09 awarded by The National Science Foundation and National Institute of Health, respectively. The government has certain rights in the invention.

This application is a continuation-in-part of U.S. patent application Ser. No. 07/695,104, filed May 3, 1991 now abandoned.

TECHNICAL FIELD

The present invention relates generally to medical research and diagnostics and, more particularly, to a method and apparatus adapted to produce spectra that are indicative of the chemical composition of tissue and in a more particular application, the inner walls of arteries in vivo.

BACKGROUND OF THE INVENTION

A number of techniques have been utilized in the past to make constituent identifications in atherosclerotic lesions. These techniques include HPLC, NMR chemical-shift imaging and immunocytochemistry. Atheroma recognition has been performed by other techniques including duplex ultrasound and pneumoplethysmography. Atheroma classification has been made by microscopic and histologic examinations. Additionally, spatial profiling has been accomplished by chemical analysis, enzymatic assays and immunofluorescence techniques.

While all of these different techniques and technologies are useful in qualitatively analyzing atherosclerotic lesions and plaques in vitro, it should be appreciated that new technologies used for treating atherosclerotic lesions and plaques require a reliable method of in vivo lesion and plaque recognition to be most effective. A need therefore exists for a reliable apparatus and method for the chemical examination of arterial endothelium and, more particularly, for analyzing the composition of atherosclerotic lesions and plaques in living tissue.

SUMMARY OF THE INVENTION

Accordingly, it is a primary object of the present invention to provide a method and apparatus for analyzing tissue and particularly arterial tissue and the lesions and plaques associated therewith in a manner overcoming the above-described limitations and disadvantages of the prior art.

Another object of the present invention is to provide an apparatus and method that may not only be used in in vitro analysis but is also adapted for in vivo analysis. Advantageously, such an apparatus and method may be utilized to not only localize lesions but to evaluate the progression of disease and the effectiveness of treatment. More particularly, by permitting the actual growth of lesions as well as the effectiveness of treatment to be studied as it is being administered, improved treatment programs may be designed.

Yet another object of the present invention is to provide a method and apparatus specifically adapted to identify different lesion types to thereby allow physicians to prescribe appropriate drugs that are more likely to provide effective treatment. This is a particularly important consideration when it is realized that some of the drugs prescribed to treat lesions have serious side effects.

Still another object is to provide a method and apparatus wherein infrared radiation of a wavelength range spanning substantially 1000-2500 nm and, more preferably, 1500-2100 nm is simultaneously focused onto the arterial endothelium under study. The reflected infrared radiation is then detected and analyzed at high speed to not only identify lesions but also evaluate the progression of disease and effectiveness of treatment.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved apparatus is provided for analyzing tissue including arterial lesions. The apparatus may not only be utilized for in vitro analysis but also, advantageously may be utilized for in vivo analysis. The apparatus comprises a light source for transmitting simultaneously and in parallel an incident beam of light of a wavelength range from 1000 to 2500 nm and more preferably from 1500 to 2100 nm. A fiber optic probe is operatively connected to the light source. A light directing or focusing mechanism is mounted to the distal end of the probe. The focusing mechanism may comprise a compound parabolic concentrator (CPC) that may, for example, be formed from plastic and include a polished aluminum lining. The CPC is similar to those designed for use for solar power concentration. The CPC is adapted to compress the incident beam from the transmitting fiber optic onto a small spot on the tissue surface undergoing analysis. Additionally, the apparatus includes detectors, such as lead sulfide detectors, for detecting the scattered light from the artery surface or other tissue being analyzed.

In an alternative embodiment, the light directing mechanism comprises an inverted, substantially conical reflector developed from both ellipsoids of rotation and paraboloids of rotation. This reflector serves to direct the incident beam from the transmitting optic fiber over the tissue undergoing analysis. Additionally, light reflected by the tissue is directed or focused into receiving optic fibers so as to allow for better detection and hence, chemical analysis of the tissue.

The apparatus further includes means for high speed parallel analyzing of the spectra reflected from the tissue and producing color images thereof. Such a means may, for example, comprise a supercomputer, such as available at the University of Kentucky, and appropriate software such as the copyrighted Best Algorithm software program developed by co-inventor, Robert A. Lodder. Further, the fiber optic probe of the apparatus is preferably adapted for introduction into a patient to thereby allow in vivo analysis of tissue and particularly the walls of arteries. This means may comprise any catheter assembly appropriate for this purpose.

In accordance with a further aspect of the present invention, a method of analyzing tissue including arterial lesions is provided. The method broadly includes the steps of focusing light on the tissue to be analyzed and detecting light reflected by the tissue. As indicated above, the light being focused is of a wavelength range from 1000 to 2500 and more preferably 1500 to 2100 nm. The method further includes a step of analyzing the spectra from the tissue and producing color images thereof. Advantageously, both the focusing and analyzing steps are performed to allow high speed data acquisition and analysis. Specifically light having a range of wavelengths from 1000 to 2500 nm and more preferably 1500 to 2100 nm is simultaneously focused in parallel at all locations being analyzed. The analysis of the reflected light is also completed simultaneously and in parallel for all locations being analyzed over the same range of wavelengths. As all tissues absorb light at all these wavelengths, with different tissues absorbing only a little more at some wavelengths than others, this broad band parallel approach is necessary to insure that no unusual tissue is missed during study. Hence, the analysis is more accurate and complete. Further, as the focusing and analysis are performed in parallel the complete study may still be completed in a sufficiently short time span to allow clinical utilization such as for arterial angiography. In accordance with a further method of analyzing arterial endothelium in vivo utilizing a fiber optic probe, the method includes the initial step of introducing the probe into an artery of a patient.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of this specification illustrates several aspects of the present invention and together with this description serves to explain the principles of the invention. In the drawing.

Reference will now be made in detail to the present preferred embodiment of the invention an example of which is illustrated in the accompanying drawing.

DETAILED DESCRIPTION OF THE INVENTION

Figure 1:
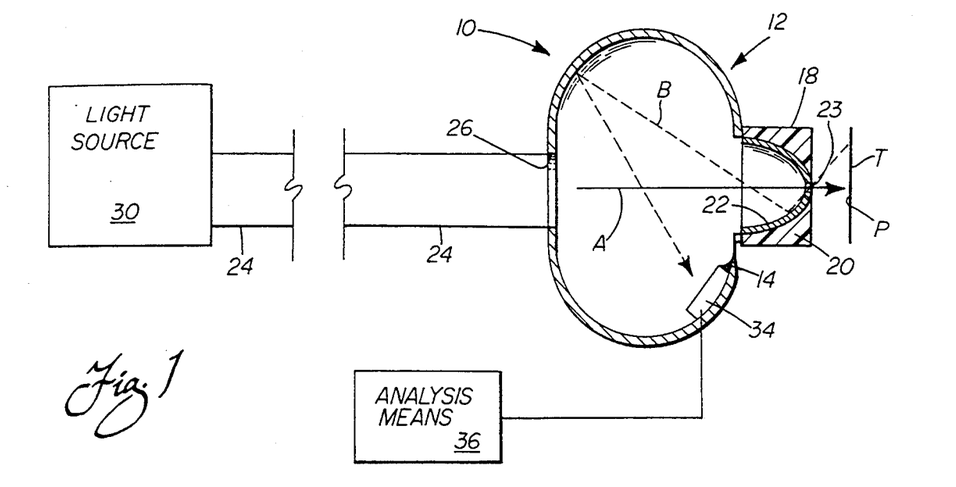
FIG. 1 is a schematical representation of one embodiment of the apparatus of the present invention including a compound parabolic concentrator for the analysis of tissue.
Figure 2:
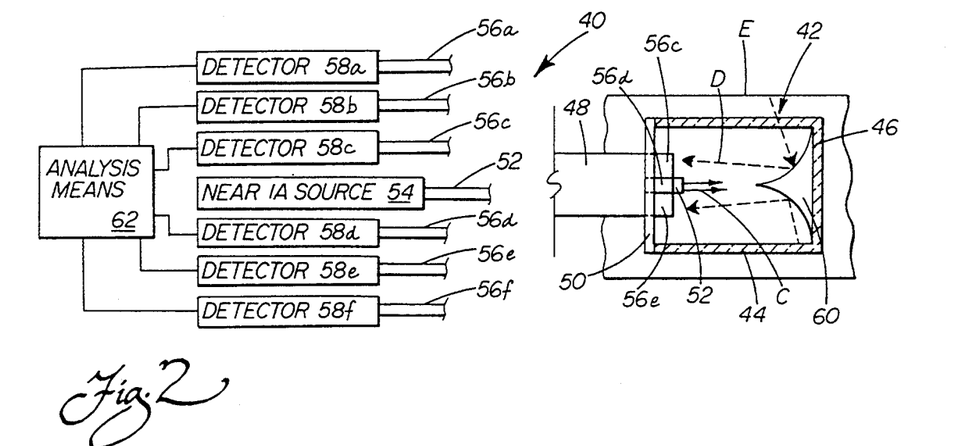
FIG. 2 is a schematical representation of a second, alternative embodiment of the present invention including an inverted, substantially cone-shaped reflector.

Reference is now made to the drawing figures showing the apparatus of the present invention for producing and detecting spectra indicative of the chemical composition of tissue undergoing analysis. Two different embodiments of the present invention are shown and described below and in the drawing figures. The first embodiment shown in FIG. 1 is described below for use in analyzing tissue in vitro. The second embodiment shown in FIG. 2 is described below for use in analyzing tissue and, more particularly, arterial endothelium, in vivo. It should be appreciated, however, that the following detailed descriptions are being presented for purposes of illustration and explanation, and accordingly, the embodiments are not to be considered as being limited to the particular applications being described.

FIG. 1 schematically shows one embodiment of the apparatus 10 of the present invention. More particularly, the apparatus 10 includes a fiber optic probe, generally designated by reference numeral 12. The probe 12 includes an integrating sphere 14 of a type known in the art and formed of any appropriate material. A compound parabolic concentrator (CPC) 18 is mounted to the integrating sphere 14. The CPC 18 includes a main body member 20 formed from plastic and a polished aluminum lining 22. As is known, the CPC 18 also includes a central optical aperture 23 through which light is directed and focused. This aperture preferably has a diameter between 0.64 and 0.84 mm$^2$ and more preferably of substantially 0.74 mm$^2$.

A fiber optic bundle 24 is rigidly mounted to and held in an inlet port 26 in the integrating sphere 14, opposite the CPC 18. The fiber optic bundle 24 (transmitting fiber optic) is operatively connected to a light source 30 (see FIG. 1). The light source 30 is particularly adapted for generating a spectrum of light having a wavelength range from 1000 to 2500 nm and, more preferably from 1500 to 2100 nm. Such a light source 30 may, for example, be a tungsten-halogen lamp with wavelength selection being accomplished utilizing a concave holographic diffraction grating.

An individual light detector 34 is mounted on the wall of the integrating sphere 14. Any appropriate detector known in the art may be utilized including a lead sulfide detector and/or an indium antimonide detector cooled with liquid nitrogen.

Light of from 1000 to 2500 nm and more preferably of from 1500 to 2100 nm from the source 30 is directed simultaneously and in parallel along the transmitting fiber optic bundle 24 to the fiber optic probe 12. There the light from the source 30 is projected as an incident beam through the integrating sphere 14, the CPC 18 and the aperture 23 onto a tissue sample T (note incident light beam depicted in full line by action arrows A). As shown even scattered light of the incident beam is redirected and is concentrated by the CPC 18 so as to be tightly focused on a point P of the tissue sample T.

A significant portion of the incident light projected onto the point P of the tissue sample T is reflected back into the CPC 18 through the aperture 23. The scattered, reflected light is shown in dash line with reference to action arrow B. As shown, the reflected light is directed by the parabolic walls of the CPC 18 into the integrating sphere 14. The integrating sphere 14 then directs the reflected light so that it falls upon the detector 34.

As shown the detector 34 is connected to a means 36 for analyzing the detected spectra and producing color images thereof. Specifically, the analysis is completed over the full wavelength range of the incident light directed upon the tissue. Thus, reflected light having a wavelength range between 1000 to 2500 nm and more preferably 1500 to 2100 nm is analyzed simultaneously and in parallel. Further, equal weighting is given to each wavelength in the analysis, unlike other methods. Hence, it should be appreciated that the present method is not equivalent to Fourier Transformation (FFT) or other data congression techniques like principal components (PCA).

To achieve this end a supercomputer may be utilized under the direction of appropriate analytical software such as the Best Algorithm software program developed at the University of Kentucky by Robert A. Lodder, a co-inventor of the present invention. The Best Algorithm software program calculates the distance of the spectrum of each point on the artery wall to the center of the distribution of an ordinary arterial wall. The user arbitrarily selects colors to denote directions of spectra in hyperspace, and hence the identity of chemical constituents. Thus, the direction is color-coded to identify particular chemical species. Additionally, the length of the vectors (in standard deviations) is proportional to the concentration of the chemical species in the artery wall at the position where the spectra were recorded.

Thus, the color images are actually color density-contour plots whose contours represent the mathematically determined probability of the tissue having a certain composition. The contours are drawn at set distances in standard deviations (SDs) from the spectra of a normal artery. As you go more and more SDs from normal, the probability of being normal (no excess LDL) is less. The relationship between SDs and probability can be looked up in a standard table of the Gaussian distribution.

All prior art SDs, such as Mahalanobis SDs, are based on the assumption that spectral clusters are normally distributed and have radial symmetry (either spheroid or ellipsoid). In contrast, the SDs of the Best Algorithm are asymmetrical. In other words, the length of an SD is different in one direction than in the opposite direction. Accordingly, the SDs of the Best Algorithm are better suited to handle asymmetrical spectral distributions in hyperspace such as produced in complex mixtures like atheromas.

EXAMPLE 1

Figure 4:
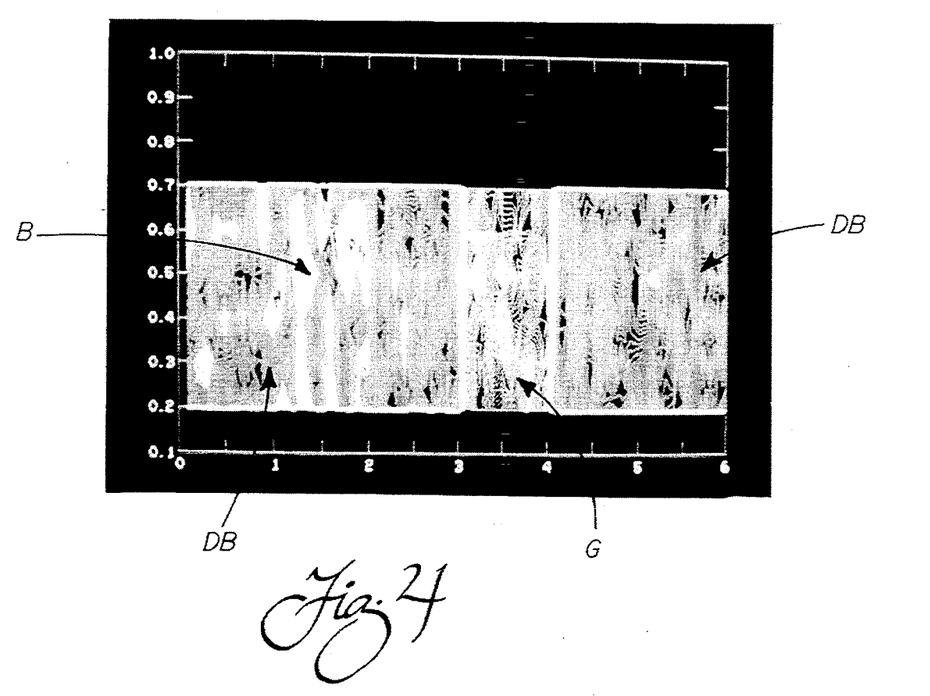
FIG. 4 is a black and white representation of a color photographic image showing the lipoprotein composition of a thoracic aorta incubated in Kreb's physiological salt solution.
Figure 5:
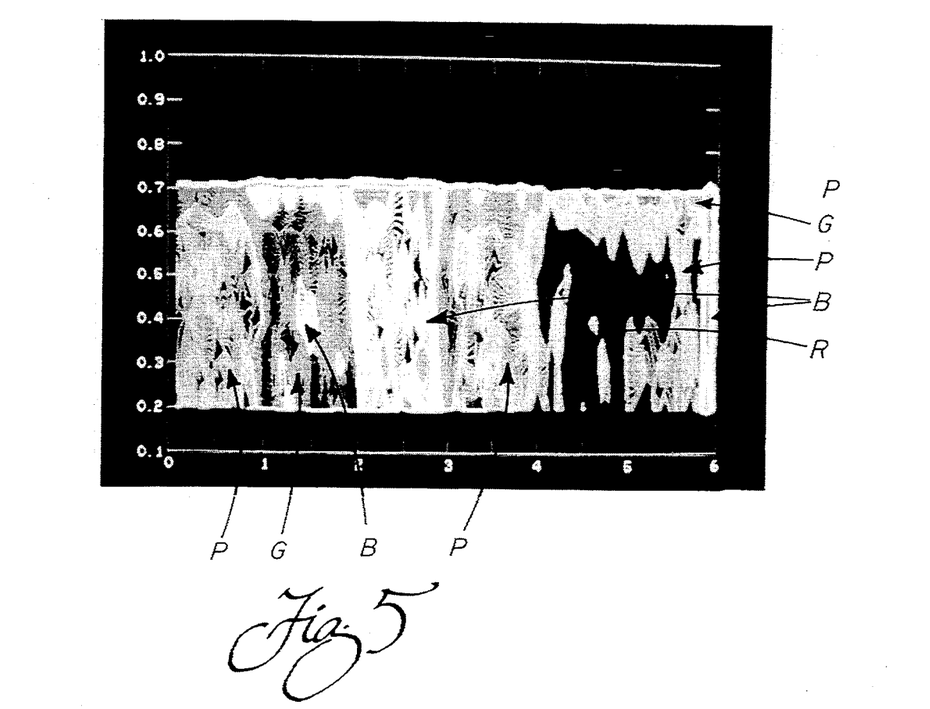
FIG. 5 is another black and white representation of a color photographic image showing the lipoprotein composition of a thoracic aorta incubated in Kreb's physiological salt solution that also contained low-density lipoprotein.

False-color "maps" as shown in FIGS. 4 and 5 were prepared as described below. The FIGS. 4 and 5 show the lipoprotein composition of thoracic aortas obtained from two laboratory rats. The aortas were each excised and partially denuded. This was done by removing the endothelium from a portion of the vessel wall of each rate. The aorta specimen shown in FIG. 4 was incubated for two hours in Kreb's physiological salt solution. The aorta specimen shown in FIG. 5 was incubated for two hours in a Kreb's physiological salt solution that also contained low density lipoprotein (LDL)(500 ug/mL).

The aortas were washed following incubation and passed beneath the CPC 18 of the probe 12 while the concentrator was held fixed. A micropositioning stage was used to allow spectra to be collected along the axis of the aorta when the aorta was opened to expose the internal surface. Both specimens were scanned along a track approximately 0.5×6 mm in dimension.

Figure 6:
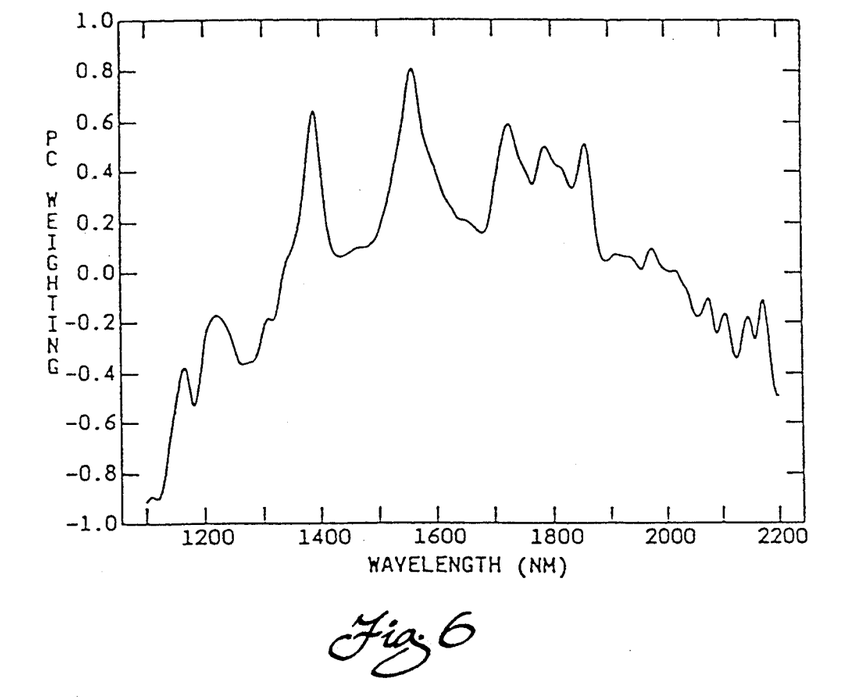
FIG. 6 is a graphical representation depicting the spectral vector of the principal axis transformation matrix corresponding to the spectral change observed in the aorta specimens incubated in low-density lipoprotein.

FIG. 6 depicts the spectral vector in the principal axis transformation matrix. This corresponds to the spectral change observed in the artery when the aorta specimen was incubated in LDL. The major spectral changes were observed near 1560 nm and between 1700 and 1870 nm.

Figure 7:
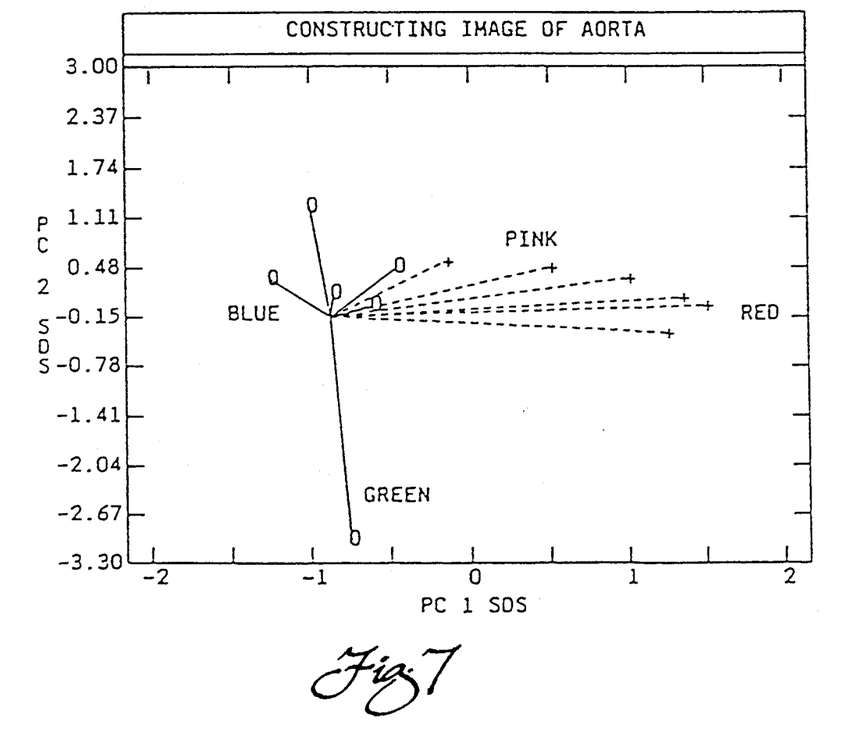
FIG. 7 is a graphical representation summarizing the process by which colors were assigned to pixels in the black and white representations of the color images of FIGS. 4 and 5.

FIG. 7 summarizes the process by which the colors were assigned to pixels in the images. The "O"s represent sample spectral obtained from the aorta incubated without LDL, and the "+"s represent sample spectra obtained from the aorta incubated in the LDL. The distances are measured in standard deviations (SDs) in spectral hyperspace between the center of aorta spectral points incubated without LDL and each test specimen spectral point (the latter point may or may not come from an aorta specimen incubated in LDL).

A parallel assimilation algorithm, R. A. Lodder, and G. M. Hiefije, *Appl. Spectrosc.*, 42, 1351–1365 (1988), was implemented on an IBM 3090-600J supercomputer to calculate the distances and assemble the results into the final color images shown as black and white representations. The center of the aorta spectral points incubated without LDL are coded dark blue (DB). Vertical motions along the solid lines in FIG. 6 (representing base-line shifts that likely correlate to vessel wall thickness) are coded green (G). Horizontal motions along the dotted lines shown in FIG. 7 (representing LDL uptake) are coded pink (P) and red (R). Red represents a larger movement in SDs than pink. The contour lines in the aortal images are drawn every 0.1 SD, and a color change occurs approximately every 3 SDs.

The image shown in FIG. 4 is predominantly blue (B) and green (G). This indicates that the aorta specimen is similar to spectra obtained from such tissues incubated without LDL. The green (G) portion is caused by a base-line shift which likely results from a thickening of the aorta wall which brings the specimen closer to the optical aperture 23.

The image shown in FIG. 5 shows nearby orthogonal changes that correspond to the uptake of LDL by the aorta wall with the red (R) color representing regions of maximum uptake of LDL. The LDL enters cells intact through receptor-mediated endocytosis (Goodman and Gilman, "The Pharmacological Basis of Therapeutics" 8th ed., Pergamon Press, 1990) and remains intact until catabolism of LDL in cellular lysosomes. The cholesteryl esters are then hydrolyzed, releasing free cholesterol and the amino acids and peptides from the degraded lipoprotein are excreted from the cell. The apolipoprotein are excreted from the cell. The apolipoprotein B spectrum and amino acids give the peaks shown in FIG. 6.

An alternative embodiment 40 of the present invention is shown in FIG. 2. In this embodiment 40, the probe 42 includes a substantially cylindrical shaped housing 44. The housing 44 is formed with a closed distal end 46 from any appropriate material including glass and, more preferably, zirconium fluoride glass.

A fiber optic bundle 48 is rigidly mounted and held in an end cap 50 that seals the proximal end of the housing 44. Preferably, the end cap 50 is also made of glass that is, for example, heat welded to the sidewall of the cylindrical housing 44.

Figure 3:
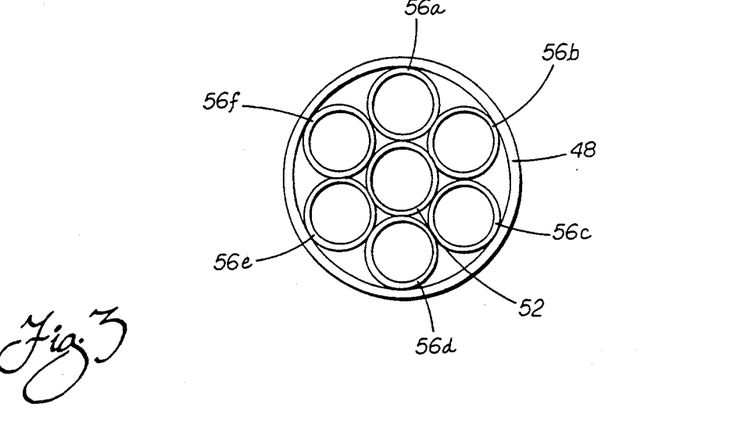
FIG. 3 is a distal end view of the fiber optic bundle used in the apparatus of the present invention.

As best shown in FIG. 3, the fiber optic bundle 48 includes seven individual fiber optic strands. A centrally disposed fiber optic strand 52 (transmitting fiber optic strand) is operatively connected to a light source 54 (see also FIG. 2). This is the same type of light source 54 described above with respect to the embodiment shown in FIG. 1. Six remaining fiber optic strands 56a–f (receiving fiber optic strands) are concentrically disposed about the central strand 52. Each of the receiving strands 56a–f is operatively connected to an individual light detector 58a–f. Once again, any type of detector 58a–f known in the art to be suitable for the purpose may be utilized (e.g. lead sulfide detectors and liquid nitrogen cooled indium antimonide detectors).

An inverted, substantially conical reflector 60 is mounted in the housing 44 adjacent the distal end 46. The reflector 60 includes a parabolically curved sidewall specifically adapted for reflecting incident light (note full line action arrows C) outwardly through the sidewall of the optically pure catheterization housing 44 and focusing that light onto the surface of the arterial endothelium undergoing in vivo analysis. Scattered light reflected from the arterial endothelium is directed by the substantially ellipsoidal sidewall of the reflector 60 back into the receiving fiber optic strands 56a–f (note dashed line action arrows D).

This light directing is furthered by having the distal end of the transmitting fiber optic strand 52 extend a short distance (between 0.1 and 50.0 mm) beyond the distal ends of the receiving fiber optic strands 56a–f as shown in FIG. 2. More specifically light is reflected downwardly from the outer sidewall of the transmitting fiber optic strand 52 into the receiving fiber optic strands 56a–f. Further, each of the receiving fiber optic strands 56a–f is effectively shaded from light reflected by the arterial endothelium at the opposite side of the artery. Hence, the resulting images are clearer than would otherwise be obtainable. The fiber optic strands 56a–f direct the reflected light to the cooperating detectors 56a–f to which the fiber optic strands are respectively operatively connected.

As indicated above with respect to the description of the embodiment shown in FIG. 1, the detectors 58a–f are operatively connected to a supercomputer 62 that provides analysis of the spectra detected by the detectors and produces color images of the arterial endothelium. These images may be utilized to determine the chemical composition of the arterial endothelium and thus, the chemical makeup of any atherosclerotic lesions and plaques thereon. Advantageously, by determining the chemical makeup of the lesions and plaques, a more effective treatment regimen may be identified and initiated. As a result, the utilization of ineffective treatment regimens for the treatment of particular types of lesions is avoided. Hence, no time is wasted in treatment and more effective and efficient treatment is provided for the improved safety and health of the patient at a lower cost.

In accordance with the method of the present invention, in vitro analysis as described with respect to the embodiment shown in FIG. 1 may be simply and easily completed. This is done as described above in Example 1 by excising and partially denuding a tissue sample from the endothelium of a portion of a artery or vessel wall. The excised tissue is incubated and washed. The tissue is then mounted on a micropositioning stage so that it may be carefully analyzed by passing beneath the optical aperture 23 of the CPC 18.

As discussed above, the CPC 18 focuses simultaneously and in parallel a limited light spectrum having a wavelength from 1000 to 2500 nm onto a small spot on the tissue sample T. More preferably, the light spectrum may have a wavelength range from 1500 to 2100 nm. This is because major spectral changes indicating the presence of low-density lipoprotein (LDL) may be observed in this range. In order to determine the presence of these low-density lipoproteins with analytical precision it is necessary to utilize light across the full spectrum indicated. This is required as all tissue absorbs light at all wavelengths across this range and different tissues absorb only a little more at some wavelengths than others. As the particular wavelength(s) where these differences occur are not known in advance, it is necessary to analyze the entire range with each wavelength being given equal weight in the analysis. Further, this must be done simultaneously and in parallel to insure a speed of imaging necessary to make this method acceptable for clinical applications. Only in this way is it possible to avoid missing the presence of unusual tissue of interest to the clinician completing the study. Of course, as indicated above the reflected light is analyzed using a supercomputer operatively controlled by appropriate software.

In accordance with a further aspect of the present invention is a method of analyzing arterial endothelium in vivo utilizing the apparatus shown, for example, in FIG. 2. In accordance with this method the probe 42 is first introduced into an artery. This may be done by any known procedure appropriate for this purpose involving incision and opening of a portion of the artery for placement of the catheter probe 42 therein. Procedures similar to those used for the completion of angioplasty operations may be used for this purpose.

After introducing the probe 42 into the artery, the probe is manipulated until it is positioned to allow analysis of the desired portions of the arterial endothelium. Once again, this positioning may be completed in accordance with standard techniques utilized in angioplasty procedures.

Once the probe 42 has been properly positioned, the method continues with the step of continuously focusing simultaneously and in parallel the near infrared light spectrum of from 1000 to 2500 nm or more preferably from 1500 to 2100 nm onto the entire area of arterial endothelium to be analyzed. Next is the detecting of the light reflected by the arterial endothelium by the detectors 58a–f. Finally, the method concludes with the step of analyzing the spectra detected from the arterial endothelium and producing color images thereof.

More specifically, the full spectrum range of light originally focused upon the arterial endothelium is detected simultaneously and in parallel and then analyzed simultaneously and in parallel. During the analysis, equal weighting is given to each wavelength so as to insure that any variations in absorbance at any wavelength for each location of tissue undergoing analysis is observed.

The present method and apparatus thereby provide spatially resolved chemical analysis resulting in the production of color images that allow the doctor or lab technician to determine the location and quantities of substances such as high density lipoprotein (HDL), low density lipoprotein (LDL), and apolipoproteins,, such as apoA-I, apoA-II and apoB, in living arterial tissue.

The result is the only known method for high speed parallel data acquisition and analysis of arterial lesions in vivo. Accurate analysis of lesions in vivo is a very important advance in the art as some types of lesions are treatable with drugs while others must be removed surgically. This method allows the lesions to be identified by type. Accordingly, unnecessary surgery for lesion removal is now avoidable. Further, time lost while undergoing ineffective drug treatments may now be significantly reduced.

Figure 8A:
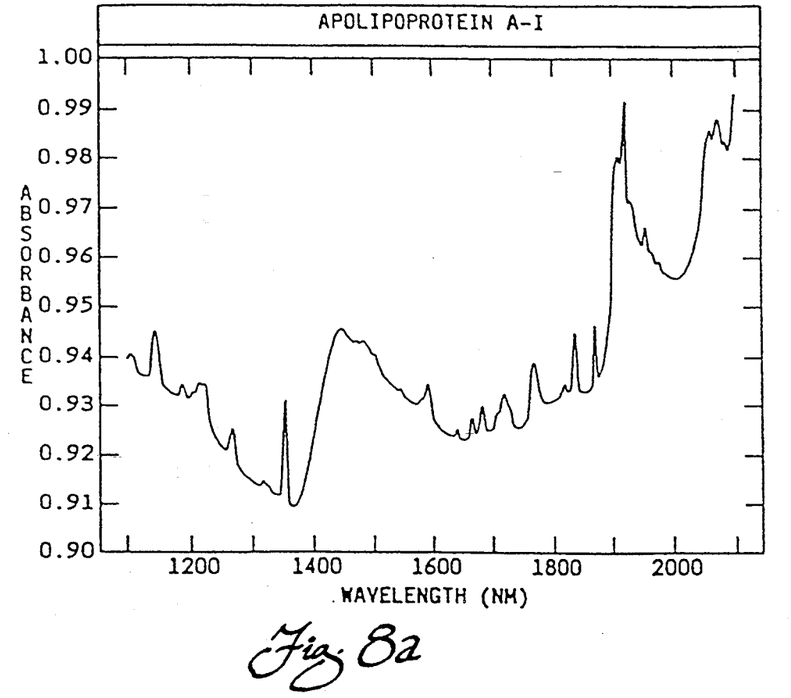
FIGS. 8a–c are NIR spectra of human apolipoproteins apoA-I, apoA-II and apoB, respectively, obtained utilizing the apparatus of the present invention.
Figure 8B:
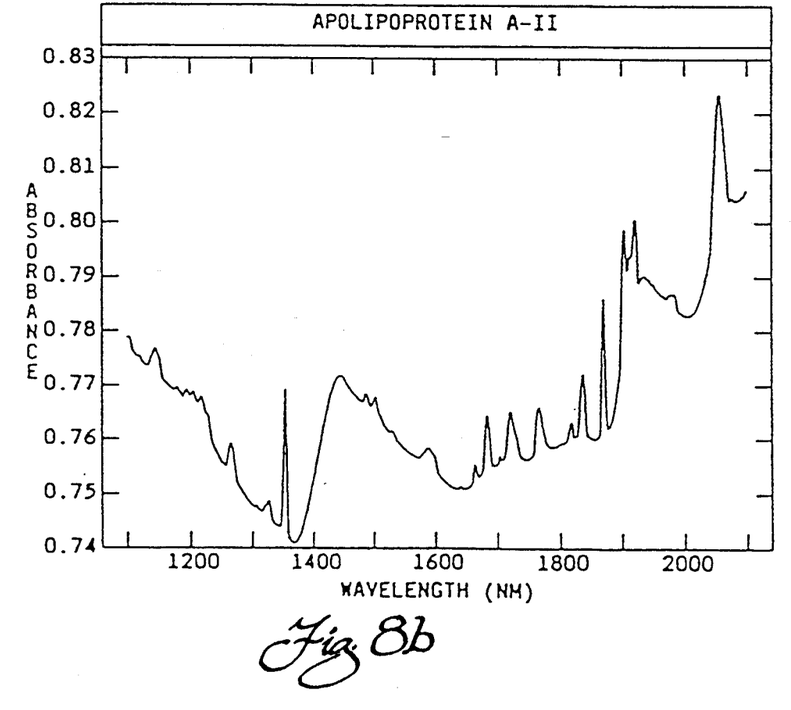
Figure 8C:
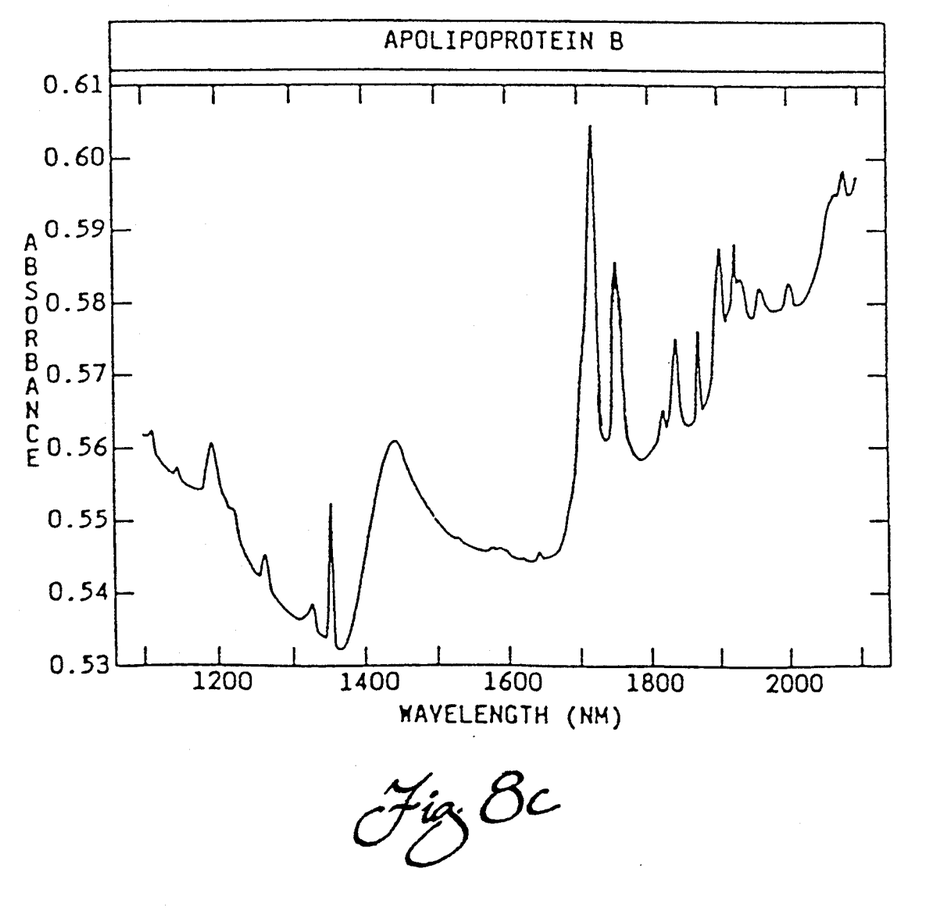

FIGS. 8a-c show near infrared spectra of human apolipoproteins apoA-I, apoA-II and apoB respectively. As should be appreciated, the distinctive spectra allow the lipoprotein substances to be identified. For example, apoA-II in HDL has a large, sharp peak near 2050 nm that is not present in the spectra for apoA-I and apoB. In contrast, apoB the main apolipoprotein in LDL has a distinctive, sharp double peak pattern at approximately 1720 and 1750 nm.

Advantageously, the ability to perform such analysis opens up a large number of possibilities including the ability to perform kinetic experiments in which the quantities of these lipoprotein and apolipoprotein substances are studied over time in a lesion. This may be done both as the lesion grows and/or as various cholesterol-lowering drugs are administered in attempts to shrink the lesion.

In summary, numerous benefits have been described which result from employing the concepts of the present invention. The apparatus of the present invention including either of the embodiments shown in FIGS. 1 or 2 may be utilized to effectively and efficiently determine the chemical composition of tissue. The procedures may be completed either in vitro or in vivo and are particularly adapted for determining the chemical composition and makeup of atherosclerotic lesions as found on the inner walls of arterial endothelium.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. An apparatus for analyzing tissue including arterial lesions, comprising:
   a light generating means for transmitting simultaneously and in parallel an incident beam of light having a wavelength range from substantially 1000 to 2500 nm;
   means for directing light from said light generating means onto the tissue to be analyzed;
   fiber-optic probe means for transmitting light from said light generating means to said light directing means and for receiving light scattered by said tissue;
   means for detecting light simultaneously and in parallel across a full wavelength range of substantially 1000 to 2500 nm scattered by said tissue; and
   means for analyzing the detected light across a full wavelength range of substantially 1000 to 2500 nm.
   said fiber opticprobe means including a centrally located light transmitting strand and a radial array of light receiving strands concentrically positioned around said light transmitting strand, said light transmitting and receiving strands each including a distal end and said distal end of said light transmitting strand projecting beyond said distal ends of said light receiving strands by between 0.1 and 50.0 mm.

2. The apparatus set forth in claim 1, wherein light from said light generating means is of a more limited wavelength range from substantially 1500 to 2100 nm and said means for detecting and analyzing light functions over a more limited wavelength range of substantially 1500 to 2100 nm.

3. The apparatus set forth in claim 1, wherein said light directing means is an inverted substantially conical reflector.

4. The apparatus set forth in claim 3, wherein said inverted substantially conical reflector includes a parabolic sidewall for scattering incident light and focusing light reflected from said tissue.

5. A method of analyzing tissue, comprising the steps of:
   focusing simultaneously and in parallel light having a continuous bandwidth range of at least 600 nm within a Wavelength range from substantially 1,000-2,500 nm on said tissue to be analyzed;
   detecting simultaneously and in parallel light having said at least 600 nm bandwidth range Within a wavelength range from substantially 1,000-2,500 nm scattered by said tissue; and
   analyzing simultaneously and in parallel the detected light having said at least 600 mm bandwidth range within a wavelength range from substantially 1,000-2,500 nm while giving all wavelengths equal weight.

6. The method set forth in claim 5, wherein said light being focused is of a more limited wavelength range from substantially 1500 to 2100 nm and said light detecting and analyzing steps are also carried out over a more limited wavelength range from substantially 1500 to 2100 nm.

7. A method of analyzing arterial endothelium in vivo utilizing a fiber optic probe, comprising the steps of:
   introducing said probe into an artery;
   focusing simultaneously and in parallel light having a continuous bandwidth range of at least 600 nm within a wavelength range from substantially 1,000-2,500 nm on said arterial endothelium to be analyzed;
   detecting simultaneously and in parallel light having said continuous bandwidth range of at least 600 nm within a wavelength range from substantially 1,000-2,500 nm as reflected by said arterial endothelium; and
   analyzing simultaneously and in parallel the detected light having said continuous bandwidth range of at least 600 nm within a wavelength range from substantially 1,000–2,500 nm while giving all wavelengths equal weight.

8. The method set forth in claim 7, wherein said light being focused is of a more limited wavelength range from substantially 1500 to 2100 nm and said detecting and analyzing steps are also carried out over a more limited wavelength range from substantially 1000 to 2500 nm.

* * * * *

UNITED STATES PATENT AND TRADEMARK OFFICE
CERTIFICATE OF CORRECTION

PATENT NO. : 5,441,053
DATED : August 15, 1995
INVENTOR(S) : Robert A. Lodder

It is certified that error appears in the above-indentified patent and that said Letters Patent is hereby corrected as shown below:

On the title page: Item [54] and Column 1, line 1,

--APPARATUS AND METHOD FOR MULTIPLE WAVELENGTH ANALYSIS OF TISSUE--

Signed and Sealed this

Fifth Day of March, 1996

Attest:

BRUCE LEHMAN

*Attesting Officer*   Commissioner of Patents and Trademarks